(12) United States Patent
Schmeink et al.

(10) Patent No.: US 8,454,491 B2
(45) Date of Patent: Jun. 4, 2013

(54) SYSTEM FOR INDUCING A SUBJECT TO FALL ASLEEP

(75) Inventors: Anke Schmeink, Aachen (DE); Robert Pinter, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 278 days.

(21) Appl. No.: 12/989,663

(22) PCT Filed: Apr. 28, 2009

(86) PCT No.: PCT/IB2009/051724
§ 371 (c)(1),
(2), (4) Date: Oct. 26, 2010

(87) PCT Pub. No.: WO2009/133517
PCT Pub. Date: Nov. 5, 2009

(65) Prior Publication Data
US 2011/0046434 A1    Feb. 24, 2011

(30) Foreign Application Priority Data

Apr. 30, 2008  (EP) .................................... 08103789

(51) Int. Cl.
*A61M 21/00*    (2006.01)
(52) U.S. Cl.
USPC ........................................................ 600/27
(58) Field of Classification Search
USPC ..................................................... 600/26–28
See application file for complete search history.

(56) References Cited

U.S. PATENT DOCUMENTS

| | | | |
|---|---|---|---|
| 4,573,449 | A | 3/1986 | Warnke |
| 5,403,261 | A | 4/1995 | Shimizu et al. |
| 6,902,296 | B2 | 6/2005 | Searfoss, III |
| 7,041,049 | B1 | 5/2006 | Raniere |
| 2005/0096555 | A1 | 5/2005 | Elliott |
| 2005/0143617 | A1 | 6/2005 | Auphan |
| 2006/0064037 | A1 | 3/2006 | Shalon et al. |
| 2007/0083079 | A1 | 4/2007 | Lee et al. |
| 2007/0173684 | A1 | 7/2007 | Elliott |

FOREIGN PATENT DOCUMENTS

| | | |
|---|---|---|
| JP | 04269972 | 9/1992 |
| WO | 2005055802 A1 | 6/2005 |
| WO | 2006054210 A1 | 6/2006 |
| WO | 2007105127 A1 | 9/2007 |

OTHER PUBLICATIONS

Ganguli et al: "Prevalence and Persistence of Sleep Complaints in a Rural Older Community Sample: The Movies Project"; JAGS, 1996, vol. 44, pp. 778-784.

Hossain et al: "The Prevalence, Cost Implications, and Management of Sleep Disorders: An Overview"; Sleep and Breathing, 2002, vol. 6, No. 2, pp. 85-102.

(Continued)

*Primary Examiner* — John Lacyk (57) ABSTRACT

A system (100) for inducing a subject (110) to fall asleep comprises a monitor (120) for monitoring heart rate and breathing rate of the subject (110), a coherence assessing device (130) coupled to the monitor (120) for assessing a degree of coherence between the heart rate and the breathing rate, and an output device (140, 150) coupled to the coherence assessing device (130). The output device (140, 150) may comprise a light pattern generator (140) for generating a light pattern (145) in view of the subject (110) based on the degree of coherence. The output device (140, 150) may alternatively or additionally comprise an instructing system (150) for instructing the subject on a breathing pattern, and wherein the instructions are given based on the degree of coherence.

11 Claims, 9 Drawing Sheets

OTHER PUBLICATIONS

Cysarz et al: "Oscillations of Heart Rate and Respiration Synchronize During Poetry Recitation"; American Journal of Physiology-Heart and Circulatory Physiology, 2004, vol. 287, pp. 579-587.

Janson et al: "Prevalence of Sleep Disturbances Among Young Adults in Three European Countries"; Sleep, vol. 18, No. 7, pp. 589-597, Jul. 1996.

Ohayon, M.: "Epidemiology of Insomnia: What We Know and What We Still Need to Learn"; Sleep Medicine Reviews, 2002, vol. 6, No. 2, pp. 97-111.

Penzel et al: "Schlafstorungen"; Gesundheitsberichterstattung Des Bundes, Heft (Issue) 27, Robert Koch Institut, Oct. 2005, 49 Page Document. (in German).

International Search Report—PCT/IB2009/-51724, Apr. 9, 2009.

SYSTEM FOR INDUCING A SUBJECT TO FALL ASLEEP

FIELD OF THE INVENTION

The invention relates to a system for inducing a subject to fall asleep, in particular a subject woken up from sleep.

BACKGROUND OF THE INVENTION

The International Classification of Sleep Disorders distinguishes more than 80 different disorders, which can be effectively treated. Problems with falling asleep or daytime sleepiness affect approximately 35 to 40% of the U.S. adult population annually and are a significant cause of morbidity and mortality. A disturbed sleep diminishes the recreation it provides to the sleeper. If bad sleep quality prevails over extended periods of time, it can lead to a bad general health condition, limited energy and stress resistance. Difficulties in falling asleep affect 6%-9% of the general population. However, especially in elderly patients the prevalence is much higher. A study investigating people aged 66-97 found difficulties initiating sleep in 26.7% of the male test subjects and in 44.1% of the female test subjects.

People with problems staying asleep report that they can fall asleep fairly well, but wake up a couple of hours later and cannot get back to sleep. Reasons can be manifold. If somebody wakes up and his thoughts keep spinning around his worries, what he experienced throughout the day and his plans for the next day etc., he will have difficulties to clear his mind and relax sufficiently in order to fall asleep again.

WO2007105127 A1 discloses a system for inducing a subject to fall to sleep, comprising a light pattern generator for generating a time varying light pattern in view of the subject. Further, the system comprises a breathing rate measuring unit for measuring a breathing frequency of the subject. In addition, the system comprises a control unit connected to the breathing rate measuring unit and the light pattern generator, for controlling the light pattern generator, such that the generated light pattern has a pattern frequency substantially between the measured breathing frequency and a pre-selected desired frequency. However, such a system may not induce sleep in the subject satisfactorily.

SUMMARY OF THE INVENTION

It is therefore an object of the invention to provide an improved system for inducing a subject to fall asleep.

According to a first aspect of the invention, a system for inducing a subject to fall asleep comprises a monitor for monitoring heart rate and breathing rate of the subject, a coherence assessing device coupled to the monitor, for assessing a degree of coherence between the heart rate and the breathing rate; and an output device coupled to the coherence assessing device for generating an output based on the degree of coherence to induce the subject to sleep.

In the process of inducing sleep according to the present invention, the heart rate as well as the breathing rate is monitored. Monitoring a single physiological parameter is not enough to deduce whether the subject is relaxed or stressed. Heart rate variability (HRV) refers to the beat-to-beat alterations in the heart rate. Under resting conditions, the heart rate of healthy individuals exhibits a periodic variation. This rhythmic phenomenon, known as respiratory sinus arrhythmia (RSA), fluctuates with the phase of respiration: cardio-acceleration during inspiration and cardio-deceleration during expiration. This way the heart rate tends to synchronize with the person's breathing activity. Therefore it is possible to derive the breathing frequency from the variations of the heart rate while the subject is relaxed. The heart rate and the breathing rate synchronize if a subject is in a positive or relaxed mood (high coherence) and de-synchronize if the subject is in a negative or stressed mood (low coherence). In the positive mood, the variation of the heart rate occurs in a sine wave manner.

According to an embodiment of the invention, the monitor comprises a sensor arranged to be unobtrusively situated under the chest of the subject, wherein the sensor is adapted for sensing signals generated by a mechanical impact and a deformation of the chest wherein the mechanical impact is created by a heartbeat and the deformation of the chest is due to breathing; and a processing unit configured for receiving the signals from the sensor and extracting the heart rate and the breathing rate of the subject.

Many people do not feel comfortable wearing electronic sensors while lying in the bed. A sensor unobtrusively situated in the bed according to the invention will not cause any inconvenience to the subject. In order to induce sleep to the subject, there is no special device introduced into a bedroom. Installing unusual or unfamiliar devices in the bedroom can induce anxieties in some persons, preventing them from sleeping. The approach of this invention is based on an insight, that the problem to promote sleep in a home setting calls for an absolutely unobtrusive and comfortable solution, because introducing intrusive technology into the bedroom—one of the most private spaces of a person—is strictly rejected by customers. This system with unobtrusive sensor further ensures that a sleeping partner of the subject is not disturbed.

According to a preferred embodiment, the sensor is a ferroelectret foil. In order to measure the heart rate and the breathing rate unobtrusively, a ferroelectret foil is put under the chest of the subject, preferably placed under his bed sheet. The foil generates an electric voltage if exposed to a mechanical pressure. When the mechanical pressure is applied to the ferroelectret foil, surface charges are displaced, thereby creating an electric voltage. The ferroelectret foil picks up the mechanical impact created by every heartbeat, as well as the chest deformation due to respiration. The respiratory action results in a low-frequency signal on which the heartbeats are superimposed as small peaks. The processing unit coupled to the sensor extracts the heart rate and the breathing rate from these signals for calculating the degree of coherence between them.

According to an embodiment of the invention, the output device comprises a light pattern generator connected to the coherence assessing device for generating a light pattern in view of the subject based on the degree of coherence, wherein the light pattern is capable of inducing sleep to the subject. Based on the degree of coherence the light pattern generator generates a light pattern which is visible to the subject and promotes relaxation to the subject and puts him to sleep.

In a preferred embodiment according to the invention, the light pattern comprises a sequence with objects having different optical properties such as shapes, colors, positions, light intensities and different velocities in different directions, so that light patterns having different optical images and different velocities can be observed by the subject in order to fall asleep.

According to another embodiment of the invention, the light pattern objects become brighter, larger and move faster at a lower degree of coherence, wherein the light pattern objects become lighter, smaller and move slower at a higher degree of coherence. After determining the degree of coherence, brightness and color of the light pattern objects can be modified depending on the degree of coherence between the heart rate and the breathing rate. At the high degree of coherence, which indicates the highly relaxed state, lighting will be dimmed down and the colors of the light pattern objects are modified towards warmer tones. On the other hand light pattern objects will be brighter, larger and move faster at low degree of coherence which distract wandering thoughts of the subject and try to relax him.

In a preferred embodiment according to the invention, the output device comprises an instructing system for instructing the subject on a breathing pattern, and wherein the instructions are given based on the degree of coherence. The breathing instructions may be given to the subject either by sound or by a mechanical stimulation. If the breathing instructions are given with the help of a loudspeaker or headphones, different tones are used for the inhale and exhale command. One complete breathing cycle would be represented by a first tone for inhalation followed by a second tone for exhalation and a pause between the first and second tones. By prolonging inhalation and exhalation phases of the breathing cycles, the frequency of the cycles will automatically go down at higher degrees of coherence. This way, a positive feedback is created. If the subject relaxes, his degree of coherence will go up, which leads to a lower frequency of the instructed breathing cycles, and this promotes further relaxation. Additionally, the volume of the signals is decreased, in order to promote sleep.

In order to achieve a maximum of unobtrusiveness, the breathing instructions are delivered with the help of a mechanical actor integrated in the bed, for example into the bed sheet. According to a preferred embodiment of the invention, the breathing instructions are generated by a mechanical actor comprising a ferroelectret foil or a piezo foil. If an electric voltage is applied to the actor, a mechanical deformation of the actor occurs and the breathing instructions are given to the subject through a mechanical stimulation. The frequency of the breathing instructions is adapted such that it becomes lower at a higher degree of coherence. Additionally at high degrees of coherence, the amplitude of the mechanical stimuli i.e., the amplitude of the mechanical vibration is faded away slowly by reducing the amplitude of the voltage applied to the actor. The actor may be located under the back of the subject. An advantage of using a ferroelectret foil as the actor for giving breathing instructions is that it can be made thin and flexible and can be integrated into a bed sheet.

According to another aspect of the invention, a method for inducing sleep in a subject comprises the steps of measuring heart rate and breathing rate of the subject; assessing a degree of coherence between the heart rate and the breathing rate; generating an output in view of the subject based on the degree of coherence; and repeating the abovementioned steps at a plurality of time intervals.

According to preferred embodiments of the invention, the output comprises a light pattern and/or breathing instructions based on the degree of coherence.

According to a further aspect of the invention, the abovementioned system is integrated into a natural installation found in a bedroom, for example an alarm clock. A seamless integration of the system into the bedroom environment is of paramount importance to make the subject feel comfortable. Integrating the system in a projection alarm clock is unobtrusive and the subject does not need an extra visible device in his bedroom. Using the projector of the alarm clock, the light patterns are projected on a wall or a ceiling and are unobtrusive to the sleeping partner.

DETAILED DESCRIPTION OF EMBODIMENTS OF THE INVENTION

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The figures are merely schematic views of preferred embodiments according to the invention. In the figures, the same reference numbers refer to equal or corresponding parts.

Figure 1:
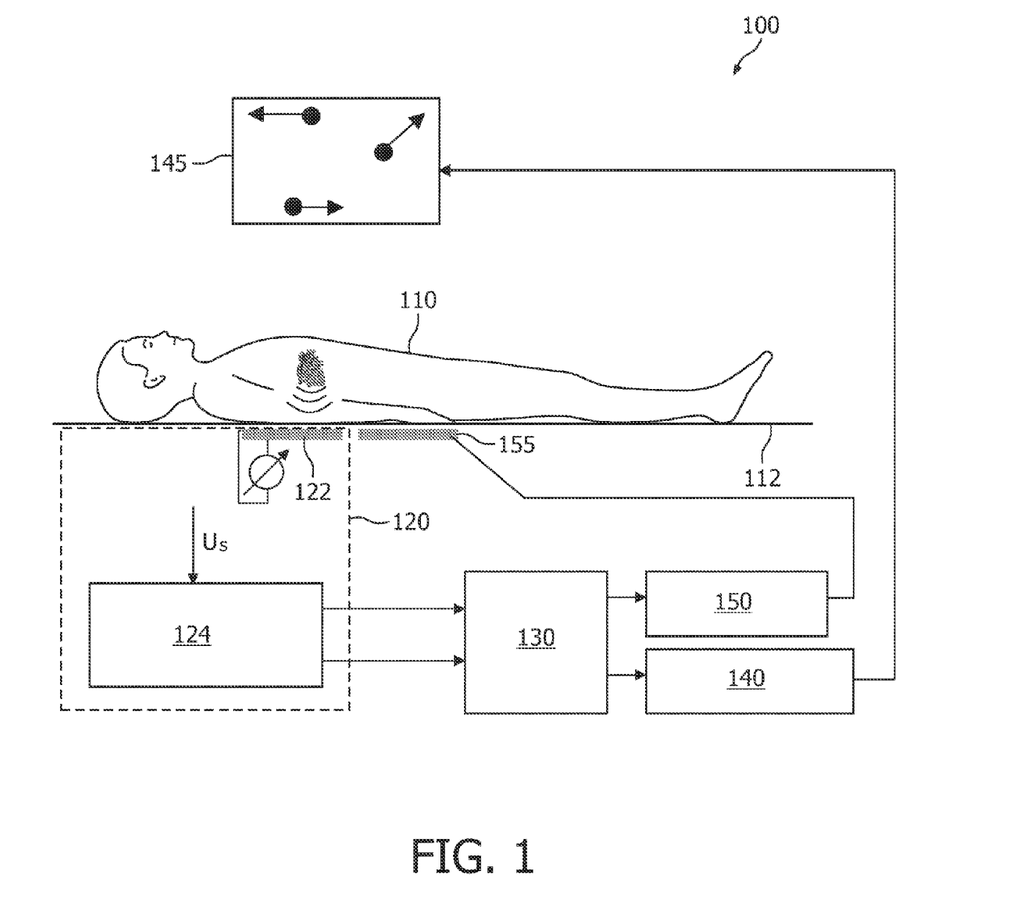
FIG. 1 illustrates an embodiment of a system for inducing a subject to fall asleep according to the invention.

FIG. 1 illustrates an embodiment of a system 100 for inducing a subject 110 to fall asleep. The system 100 comprises a monitor 120 for monitoring heart rate and breathing rate of the subject 110. The monitor comprises a sensor 122 and a processing unit 124. The sensor 122 is unobtrusively situated under the chest of the subject 110 under his bed sheet 112. The sensor 122 is a ferroelectret foil or a piezo foil. Further, the system 100 comprises a device 130 for assessing a degree of coherence between the heart rate and the breathing rate. A light pattern generator 140 is connected to the device 130. It generates a light pattern 145 in view of the subject 110. The system 100 also comprises an instructing system 150 for instructing the subject how to breathe by generating breathing instructions to the subject 110 through an actor 155 placed under the bed sheet 112.

FIG. 1 depicts an unobtrusive vital parameter measurement used for inducing sleep to the subject 110 by manipulating direction, brightness, color and velocity of projected light pattern 145 and/or through breathing instructions given by the actor 155. The light pattern generator 140 comprises means for projecting a light pattern on a surface, such as a screen, wall and/or a ceiling which is in view of the subject 110, so that the subject 110 can observe the light pattern that is generated. In order to measure the heart rate and the breathing rate unobtrusively, the ferroelectret foil 122 is put under the bed sheet 112. The ferroelectret foil 122 generates an electric voltage if exposed to mechanical pressure. It picks up the mechanical impact created by every heartbeat, as well as the chest deformation due to respiration. It was found that the respiratory action results in a low-frequency signal on which the heartbeats are superimposed as small peaks.

Monitoring Heart Rate and Breathing Rate:

Heart rate variability (HRV) refers to the beat-to-beat alterations in heart rate. Under resting conditions, the heart rate of healthy individuals exhibits a periodic variation. This rhythmic phenomenon, known as respiratory sinus arrhythmia (RSA), fluctuates with the phase of respiration: cardio-acceleration during inspiration and cardio-deceleration during expiration. This way the heart rate tends to synchronize with the person's breathing activity under resting conditions. Therefore it is possible to derive the breathing frequency from the variations of the heart rate.

Figure 2:
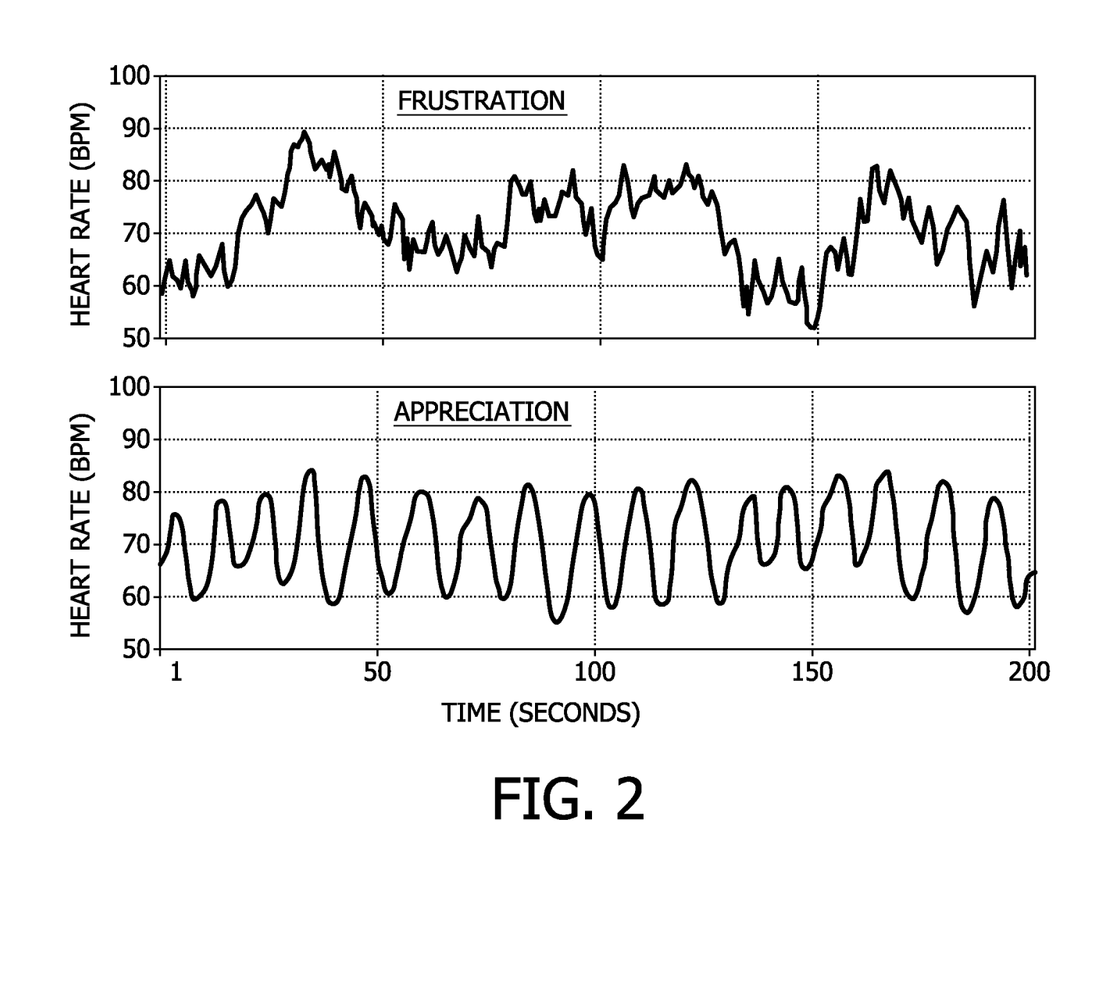
FIG. 2 illustrates a degree of coherence of heart rate and breathing rate of a subject in different moods.

FIG. 2 shows synchronization of the heart rate and the breathing rate when the subject is in a positive or relaxed mood (high coherence), compared to the de-synchronization found when the subject is in a negative or stressed mood (low coherence). In the positive mood, the variation of the heart rate occurs in a sine wave manner.

Figure 3A:
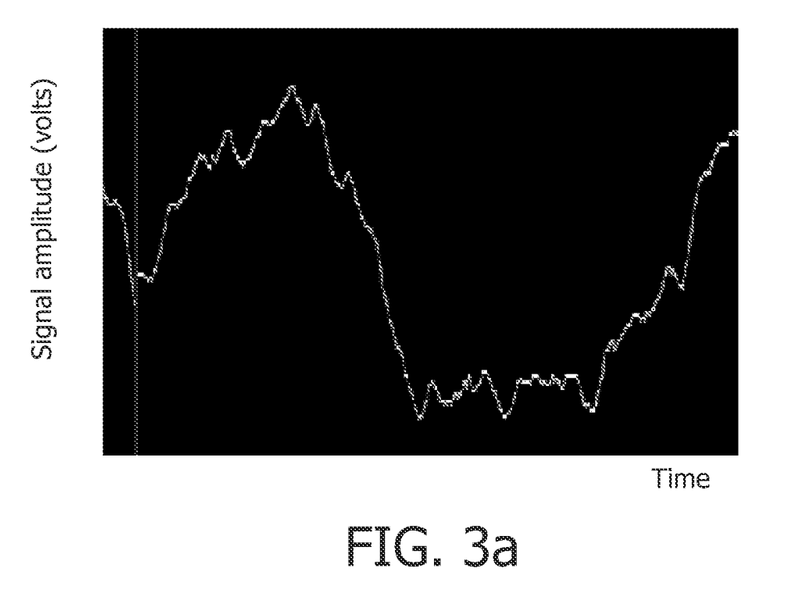
FIG. 3a illustrates an example reading of a signal $U_s$ generated by a ferroelectret foil situated under the bed sheet of a subject.
Figure 3B:
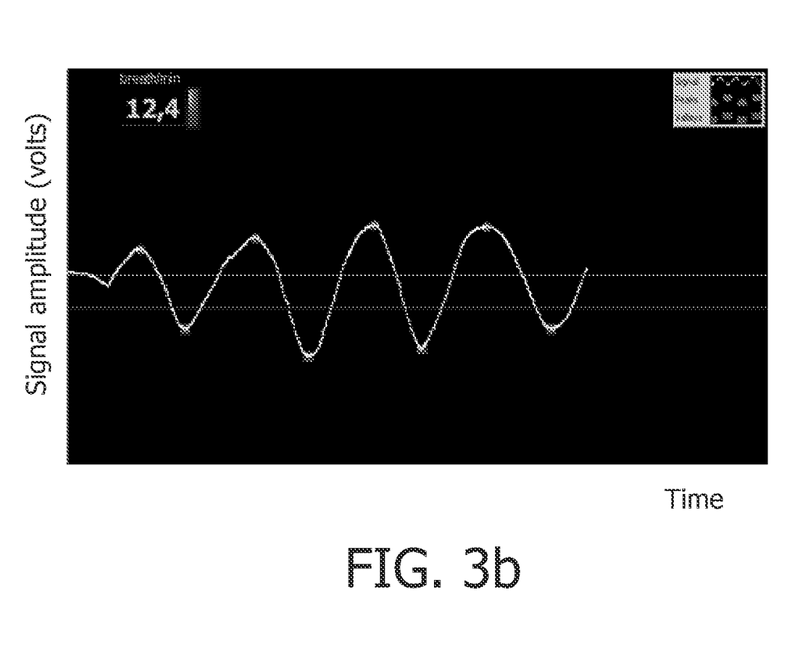
FIG. 3b illustrates a respiratory component obtained from a ferroelectret foil signal by a low-pass filtering.
Figure 4:
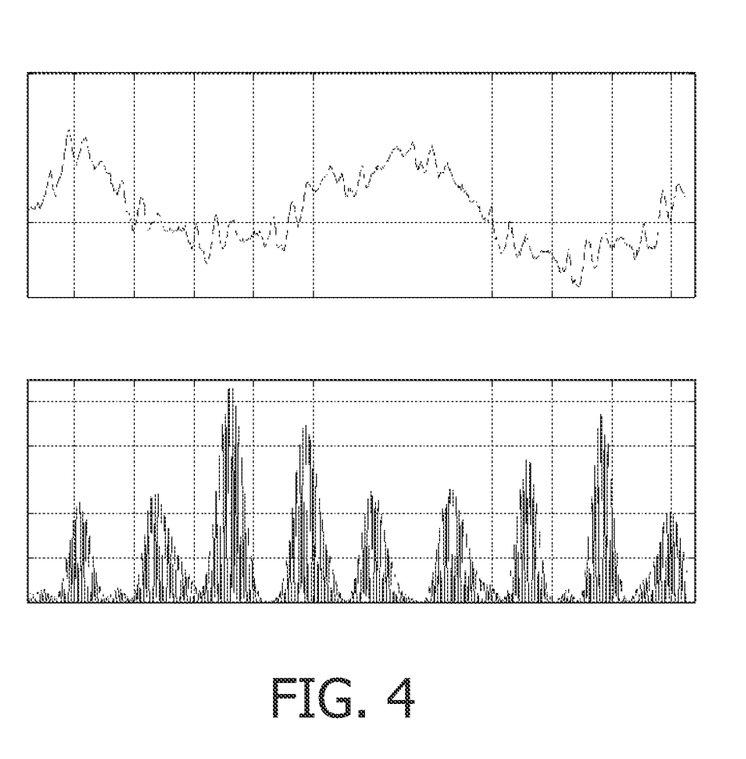
FIG. 4 illustrates a heart beat component obtained from a ferroelectret foil signal with help of a correlation technique.

The voltage generated by the ferroelectret foil 122 is the superposition of a component representing the low-frequency respiratory action and another component representing the heartbeat-induced impulses. FIG. 3a illustrates an example signal $U_s$ as measured by the ferroelectret foil 122 situated underneath the bed sheet 112. In the unprocessed signal shown in FIG. 3a, the two signal components are discernible. The low-frequency respiratory component can be easily extracted by low-pass filtering of the signal, because the respiratory frequency is significantly lower than the heart rate. The result is shown in FIG. 3b. The signal component related to the heartbeats can be extracted from the signal delivered by the ferroelectret foil 122 with the help of a correlation technique by the processing unit 124. FIG. 4 shows an unprocessed foil signal in the upper trace whereas the lower trace is the result of calculating an auto-correlation function of the signal in the time domain. The heartbeat-induced peaks visible in the unprocessed signal are clearly marked by the maxima in the auto-correlation function.

Figure 5A:
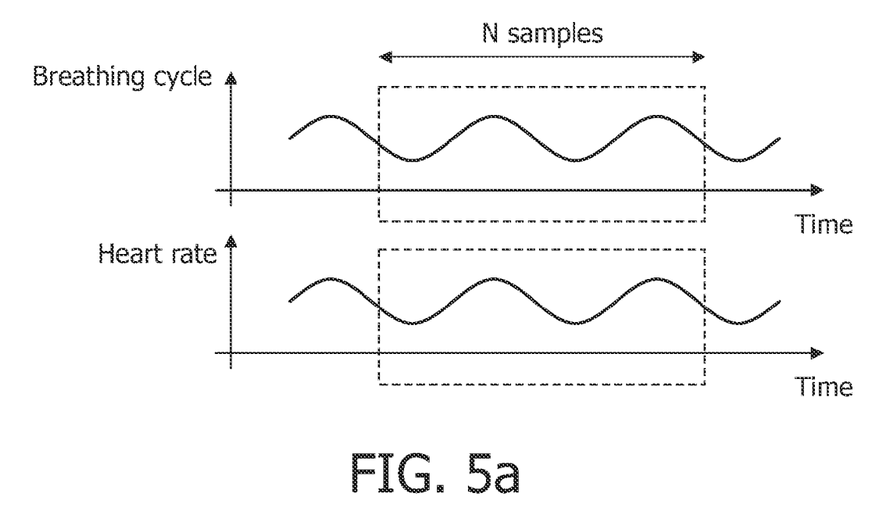
FIG. 5a and FIG. 5b illustrate a calculation of degree of coherence between the heart rate and breathing rate.
Figure 5B:
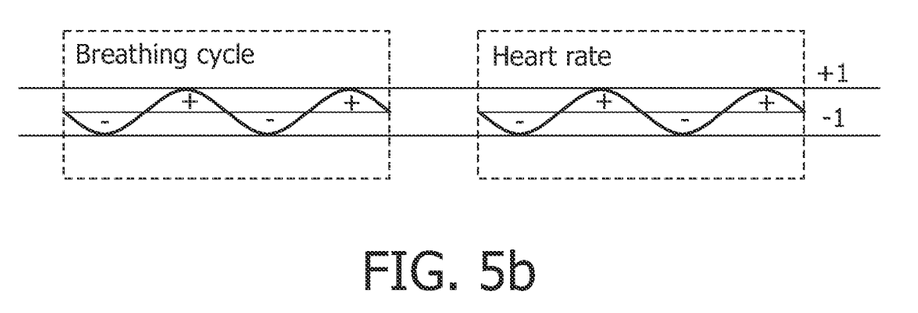

Calculation of the Degree of Coherence:

After the heart rate component is separated from the breathing rate component, the degree of coherence between the two components is determined, as shown in FIG. 5a and FIG. 5b. A segment of N samples is taken from both components, and the following calculation is applied:

$$\text{coherence} = \sum_{i=0}^{N-1} \text{respiration}(i) \cdot \text{heartrate}(i)$$

If the maxima in the respiratory signal coincide with the maxima in the heart rate signal, as it is shown in FIG. 5a, the calculated degree of coherence is high, because positive values from one segment are multiplied with positive values from the other segment, and negative values from one segment are multiplied with negative values from the other segment. So in this case, all elements contributing to the sum calculation are positive. If maxima in one segment coincide with minima in the other segment, the sum result is smaller in this case, because then positive values from the one segment are multiplied with negative values from the other segment, giving negative contributions to the sum calculation.

Figure 6:
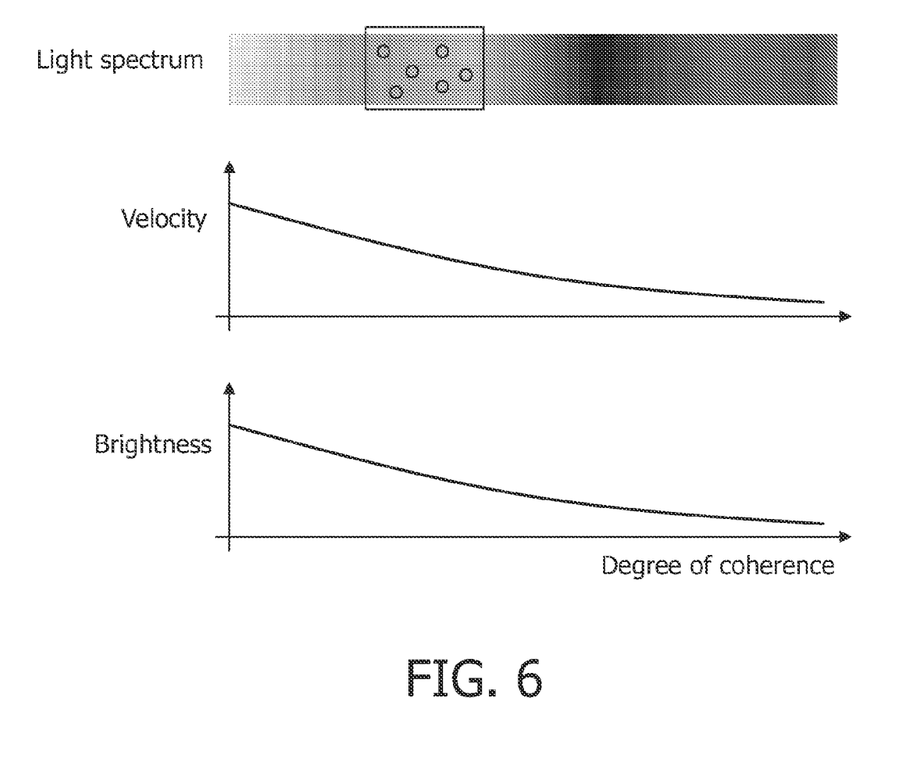
FIG. 6 illustrates a strategy for adapting velocity, color and brightness of the projected light pattern, depending on the degree of coherence.

Generating Light Patterns:

After determining the degree of coherence, it is translated into spectrum, velocity and brightness of the light pattern as shown in FIG. 6. Lighting will be dimmed down and the light colors are modified towards warmer tones improving thereby a person's relaxation status. Similarly, the velocity of the moving objects of the light pattern is reduced as the degree of coherence between the heart rate and the breathing rate becomes high. This positive feedback results in a highly effective procedure of getting back to sleep.

Figure 7:
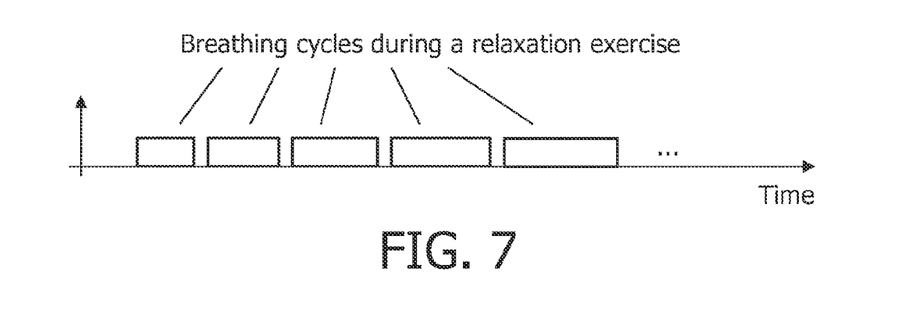
FIG. 7 illustrates a macrostructure of a relaxation exercise: slowly decreasing the frequency of breathing cycles and prolonging the cycle duration.

Generating Breathing Instructions:

In general, all breathing techniques, targeting at an increased level of relaxation, prescribe a deep and slow breath. For the macrostructure of the breathing pattern, it is therefore proposed to slowly decrease the frequency of the breathing cycles over time during any relaxation exercise, as shown in FIG. 7, and to prolong the duration of the cycles.

With the help of the ferroelectret foil 155 instructions shall be given to the subject 110 as to how he or she should breathe. This means that the instructions come as a mechanical stimulation. For the microstructure of this stimulation during each breathing cycle, various patterns are conceivable, which are outlined in FIGS. 8a to 8d. All the patterns described in these figures and any combinations thereof are conceivable for the stimulation. However, the stimulation pattern presented in FIG. 8d is the preferred one in the context of this invention.

Figure 8A:
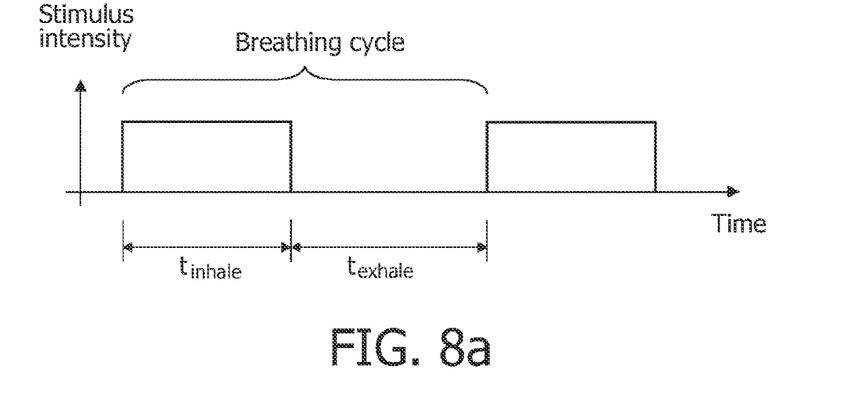
FIG. 8a illustrates a simple binary stimulation with inhalation time and exhalation time as parameters; absence of stimulus during exhalation.
Figure 8B:
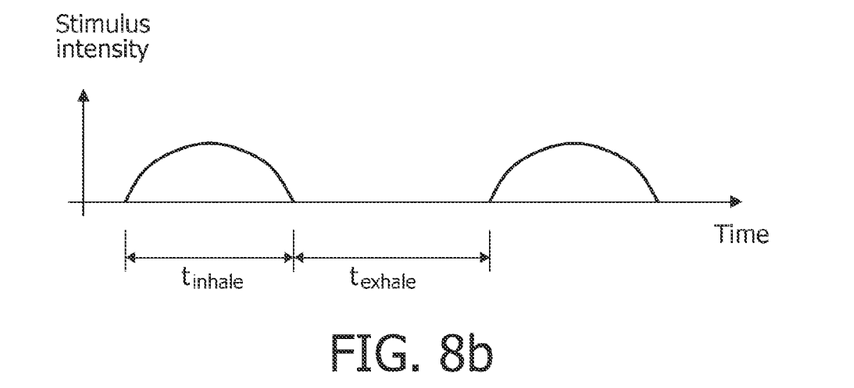
FIG. 8b illustrates an advanced stimulation with gradually varying stimulus intensity; absence of stimulus during exhalation.
Figure 8C:
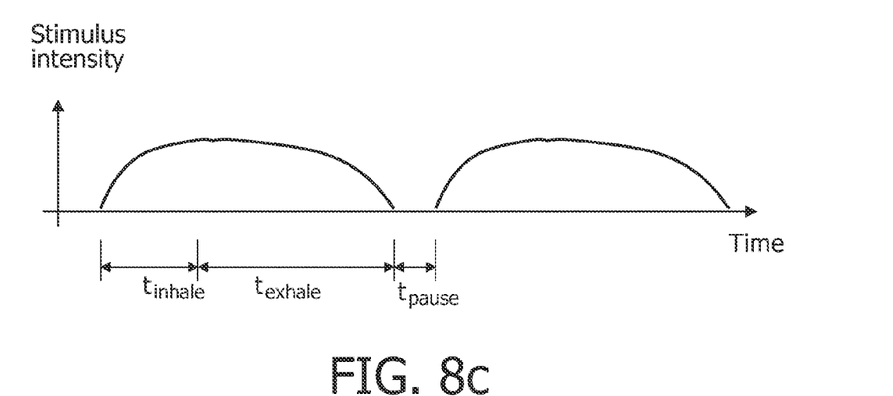
FIG. 8c illustrates an advanced asymmetric stimulation with gradually varying stimulus intensity; increasing intensity during inhalation, decreasing intensity during exhalation, allowing the introduction of breathing pauses with no stimulation.
Figure 8D:
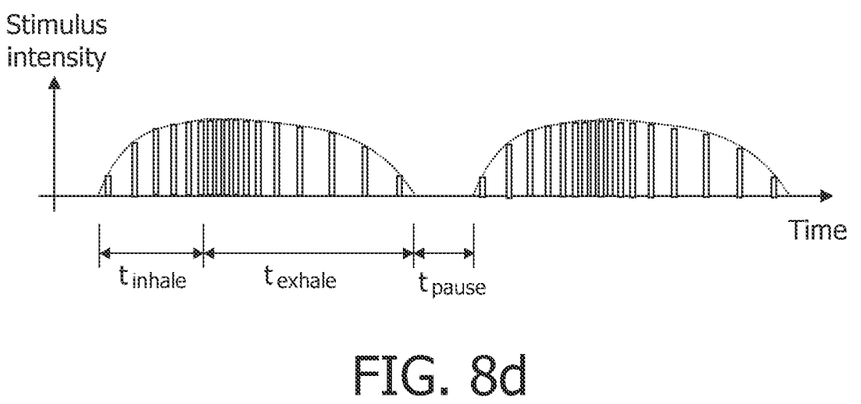
FIG. 8d illustrates a most advanced asymmetric stimulation with gradually varying stimulus intensity and varying stimulus frequency, the additional frequency coding allowing the user to better recognize the turning point from inhalation to exhalation.

The pattern shown in FIG. 8d allows the use of pauses between the breathing cycles. It furthermore allows the subject 110 to easily identify where in the breathing cycle he currently is, because that is doubly coded. Firstly, it is given by the varying amplitude of the stimuli. Secondly, the stimuli are not delivered continuously, but as bursts or impulses, as shown in FIG. 8d, and the repetition frequency of the bursts or impulses also varies.

Figure 9:
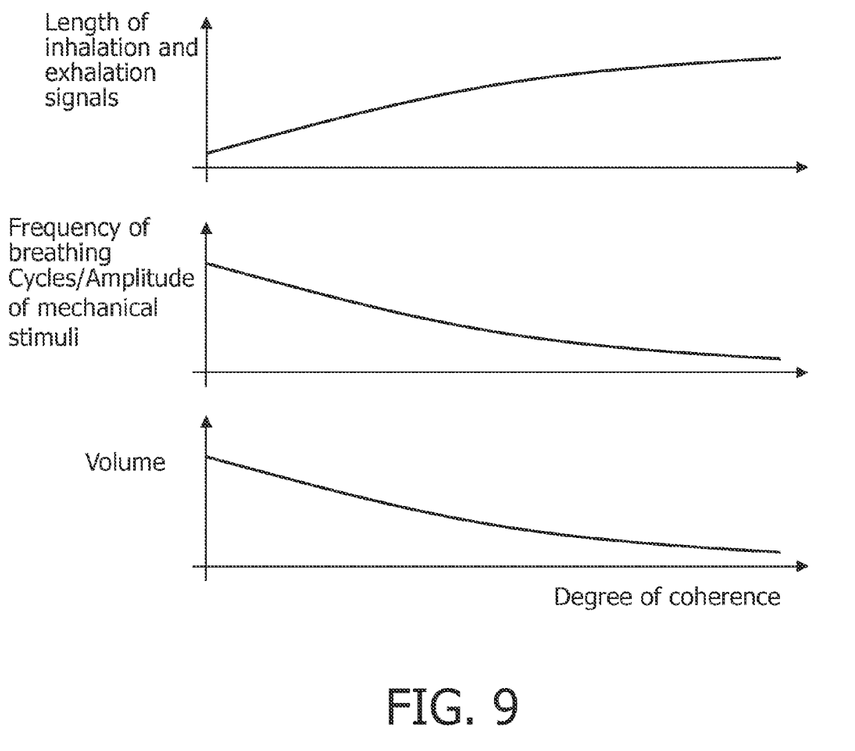
FIG. 9 illustrates a strategy for adapting the length of inhalation and exhalation phases, the frequency of the instructed breathing cycles, the amplitude of the mechanical stimulation/vibration signals, and the volume of the acoustic signals, depending on the degree of coherence.

If the breathing instructions are given with the help of the actor 155 by means of a mechanical stimulation, the frequency of the breathing instructions becomes lower at higher degrees of coherence as shown in FIG. 9. Additionally, the amplitude of the stimuli that are used is also faded away, i.e. the amplitude of the mechanical vibration is reduced by reducing the amplitude of the voltage applied to the foil actor 155. The actor 155 is a ferroelectret foil or a piezo foil. If a mechanical force is applied to the foil, surface charges are displaced, thereby creating an electric voltage. Reversely, if an electric voltage is applied to the foil, a mechanical deformation of the foil results. In other words, the ferroelectret foil acts as both a sensor 122 and an actor 155. An electric voltage is applied to the ferroelectret foil 155 which is integrated into the bed sheet 112, in order to give the breathing instructions through the vibration. The characteristic of this vibration is determined by the nature of the voltage which is applied.

If the breathing instructions are given with the help of a loudspeaker or headphones (not shown), different tones for the inhale and exhale command are used. One complete breathing cycle would be represented by the first tone for inhalation, followed by the second tone for exhalation and a pause between them. By prolonging inhalation and exhalation phases of the prescribed breathing cycles, the frequency of the cycles will automatically go down at higher degrees of coherence. This way, a positive feedback is created. When the subject relaxes, his degree of coherence will go up, which leads to a lower frequency of the instructed breathing cycles, and this promotes further relaxation. Additionally, the volume of the signals is decreased in order to promote falling asleep as shown in FIG. 9

Figure 10:
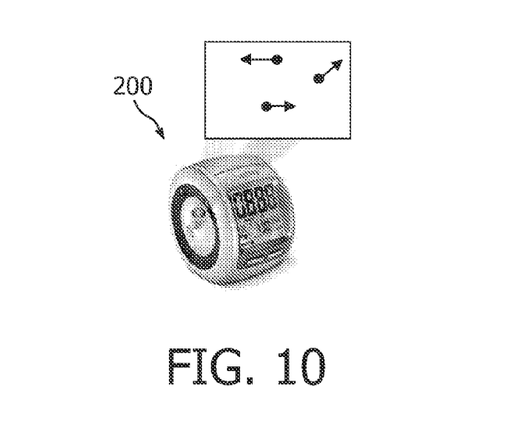
FIG. 10 illustrates an article including the system of FIG. 1.

The system of FIG. 1 may be integrated into an article such as an alarm clock, e.g. Philips AJ3600 Projection Radio Alarm Clock as depicted in FIG. 10. The light pattern generator of the system comprises means for projecting a light pattern on a surface, such as a screen, wall and/or a ceiling which is in view of the subject 110, so that the subject 110 can observe the light pattern that is generated. The moving patterns calm down the woken up person and keep his mind from spinning around worries.

It should be noted that the abovementioned strategies are given as examples. Whilst specific embodiments of the invention have been described above, it will be appreciated that the invention may be practiced otherwise than as described. A single suitably programmed processor or other unit may fulfill the functions of several items recited in the claims. The mere fact that certain measures are recited in mutually different dependent claims does not indicate that a combination of these measured cannot be used to advantage. Any reference signs in the claims shall not be construed as limiting the scope.

The invention claimed is:

1. A system for inducing a subject to fall asleep, comprising:
    a monitor for monitoring heart rate and breathing rate of the subject;
    a coherence assessing device (130) coupled to the monitor (120) for assessing a degree of coherence between the heart rate and the breathing rate, wherein said degree of coherence is determined by:
        i. separating a breathing frequency signal component of said subject from a heart rate signal component of said subject;
        ii. extracting N samples from each of the breathing frequency component and heart rate components;
        iii. calculating said degree of coherence as:

$$\text{coherence} = \sum_{i=0}^{N-1} \text{respiration}(i) \cdot \text{heartrate}(i);$$

and
    an output device coupled to the coherence assessing device for generating an output based on the degree of coherence to induce the subject to sleep.

2. A system as claimed in claim 1, wherein the output device comprises a light pattern generator coupled to the coherence assessing device for generating a light pattern in view of the subject based on the degree of coherence, wherein the light pattern is capable of inducing sleep to the subject.

3. The system of claim 1, wherein the monitor comprises:
    a sensor arranged to be unobtrusively situated under the chest of the subject, wherein the sensor is adapted for sensing signals generated by a mechanical impact and a deformation of the chest wherein the mechanical impact is created by a heartbeat and the deformation of the chest is due to breathing; and
    a processing unit configured for receiving the signals from the sensor and extracting the heart rate and the breathing rate of the subject.

4. The system of claim 3, wherein the sensor is a ferroelectret foil or a piezo foil.

5. The system of claim 2, wherein the light pattern (145) comprises a sequence with objects having different shapes, colors, positions, velocities and light intensities.

6. The system of claim 2, wherein the light pattern objects become brighter, larger and move faster at a lower degree of coherence, whereas the light pattern objects become lighter, smaller and move slower at a higher degree of coherence.

7. The system of claim 1, wherein the output device comprises an instructing system for instructing the subject on a breathing pattern, and wherein the instructions are given based on the degree of coherence.

8. The system of claim 7, wherein the breathing instructions are generated by a mechanical actor comprising a ferroelectret foil or a piezo foil.

9. A method for inducing sleep in a subject, comprising the steps of:
    i. measuring heart rate and breathing rate of the subject;
    ii. assessing a degree of coherence between the heart rate and the breathing rate;
    wherein said degree of coherence is determined by:
        j. separating a breathing frequency signal component of said subject from a heart rate signal component of said subject;
        iv. extracting N samples from each of the breathing frequency component and heart rate components;
        v. calculating said degree of coherence as:

$$\text{coherence} = \sum_{i=0}^{N-1} \text{respiration}(i) \cdot \text{heartrate}(i)$$

iii. generating an output based on the degree of coherence to induce the subject to sleep; and
    iv. repeating the steps i to iii at a plurality of time intervals.

10. A method for inducing sleep as claimed in claim 9, wherein the output is a light pattern in view of the subject.

11. A method for inducing sleep as claimed in claim 9, wherein the output comprises breathing instructions based on the degree of coherence.

* * * * *